(12) United States Patent
Stewart

(10) Patent No.: US 8,684,344 B2
(45) Date of Patent: Apr. 1, 2014

(54) ANTIBACTERIAL PROTECTIVE ENVELOPE

(76) Inventor: Pierre Stewart, Edmonton (CA)

( * ) Notice: Subject to any disclaimer, the term of this patent is extended or adjusted under 35 U.S.C. 154(b) by 359 days.

(21) Appl. No.: 13/137,176

(22) Filed: Jul. 26, 2011

(65) Prior Publication Data
US 2012/0024473 A1 Feb. 2, 2012

(51) Int. Cl.
*B25B 11/00* (2006.01)
(52) U.S. Cl.
USPC .............................. 269/21; 269/20; 156/285
(58) Field of Classification Search
USPC .................. 269/21, 20, 289 R; 156/285
See application file for complete search history.

(56) References Cited

U.S. PATENT DOCUMENTS

| | | | | |
|---|---|---|---|---|
| 5,225,027 A | * | 7/1993 | Diekwisch ..................... | 156/382 |
| 5,273,615 A | * | 12/1993 | Asetta et al. .................. | 156/750 |
| 6,286,825 B1 | * | 9/2001 | Tseng et al. ................... | 269/287 |
| 6,638,389 B2 | * | 10/2003 | Kassir et al. .................. | 156/286 |
| 7,765,682 B2 | * | 8/2010 | Hwang et al. ................... | 29/729 |
| 2012/0024473 A1 | * | 2/2012 | Stewart .......................... | 156/285 |
| 2013/0093297 A1 | * | 4/2013 | Guan et al. .................... | 312/204 |

\* cited by examiner

*Primary Examiner* — Lee D Wilson

(57) ABSTRACT

A protective envelope for a lid of a plastic cup comprises a vacuous plastic film stuck on the top of the lid which was beforehand vaporized by an antiseptic liquid, without alcohol, then dried. The plastic film includes a detachable part, activated by a thread to be pulled, which is positioned above the opening to drink of the lid. So, when a consumer is ready to drink, he removes the detachable part by pulling the thread, so freeing the opening to drink. With such protection the lid is protected from bacteria and virus which can cause diseases. In brief, the steps of conception of the antiseptic lid are: to vaporize the lid with an antiseptic liquid without alcohol, to dry the lid, to put a thin film of plastic onto the lid by positioning the detachable part over the drink opening and to stick the film onto the lid by means of a vacuum.

7 Claims, 4 Drawing Sheets

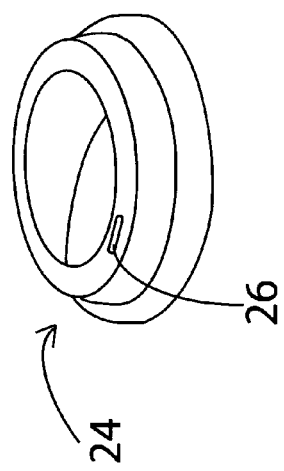
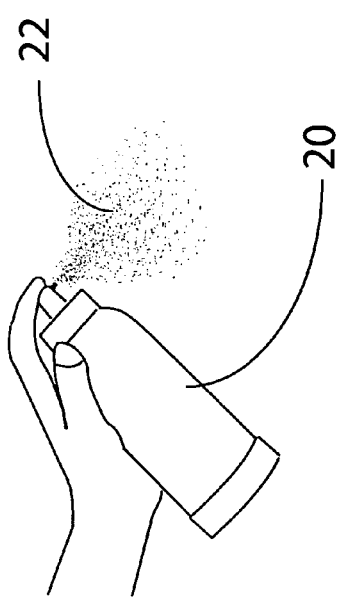
FIG. 1
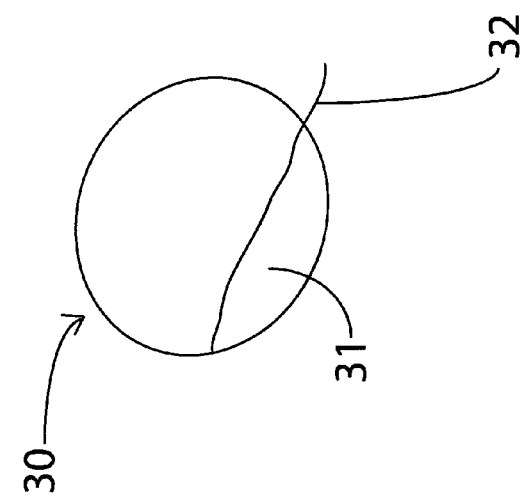
FIG. 2
FIG. 4
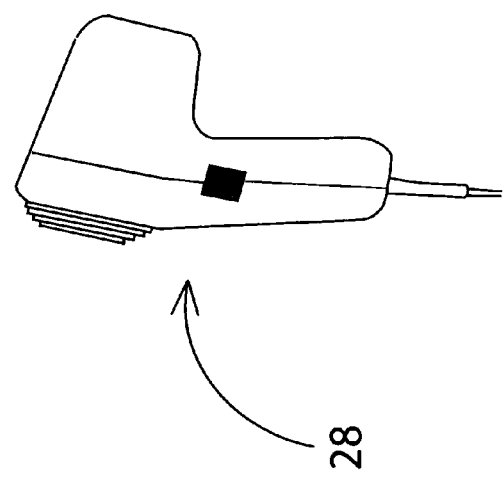
FIG. 3

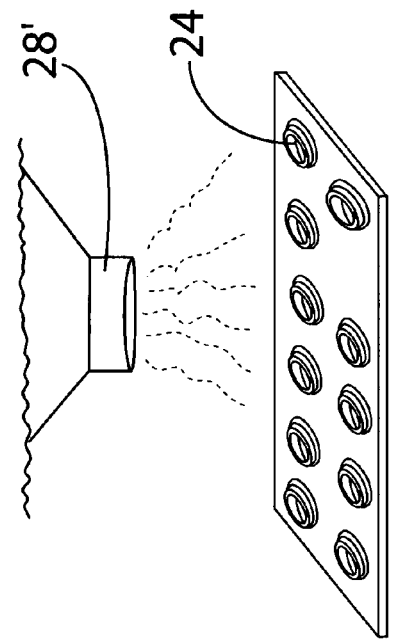
FIG. 6.2
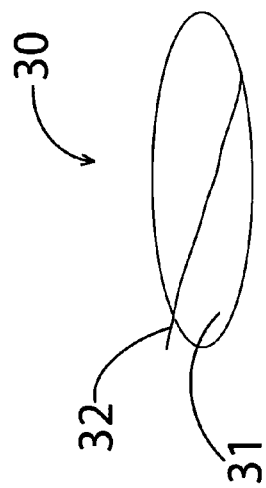
FIG. 6.4
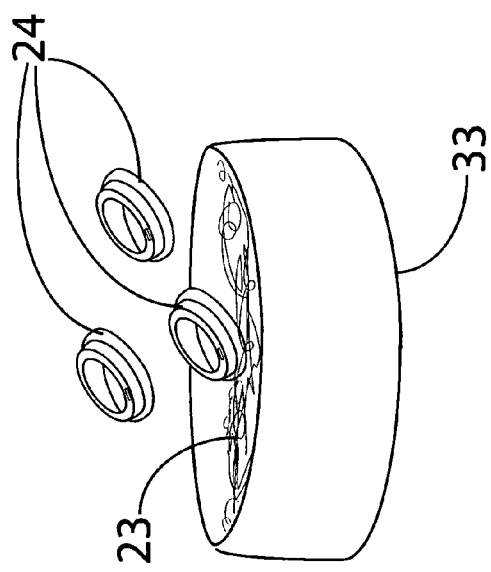
FIG. 6.1
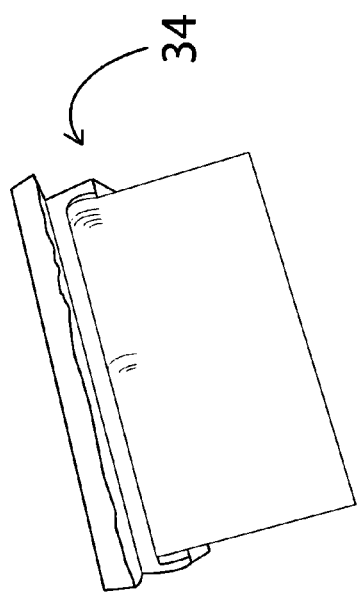
FIG. 6.3

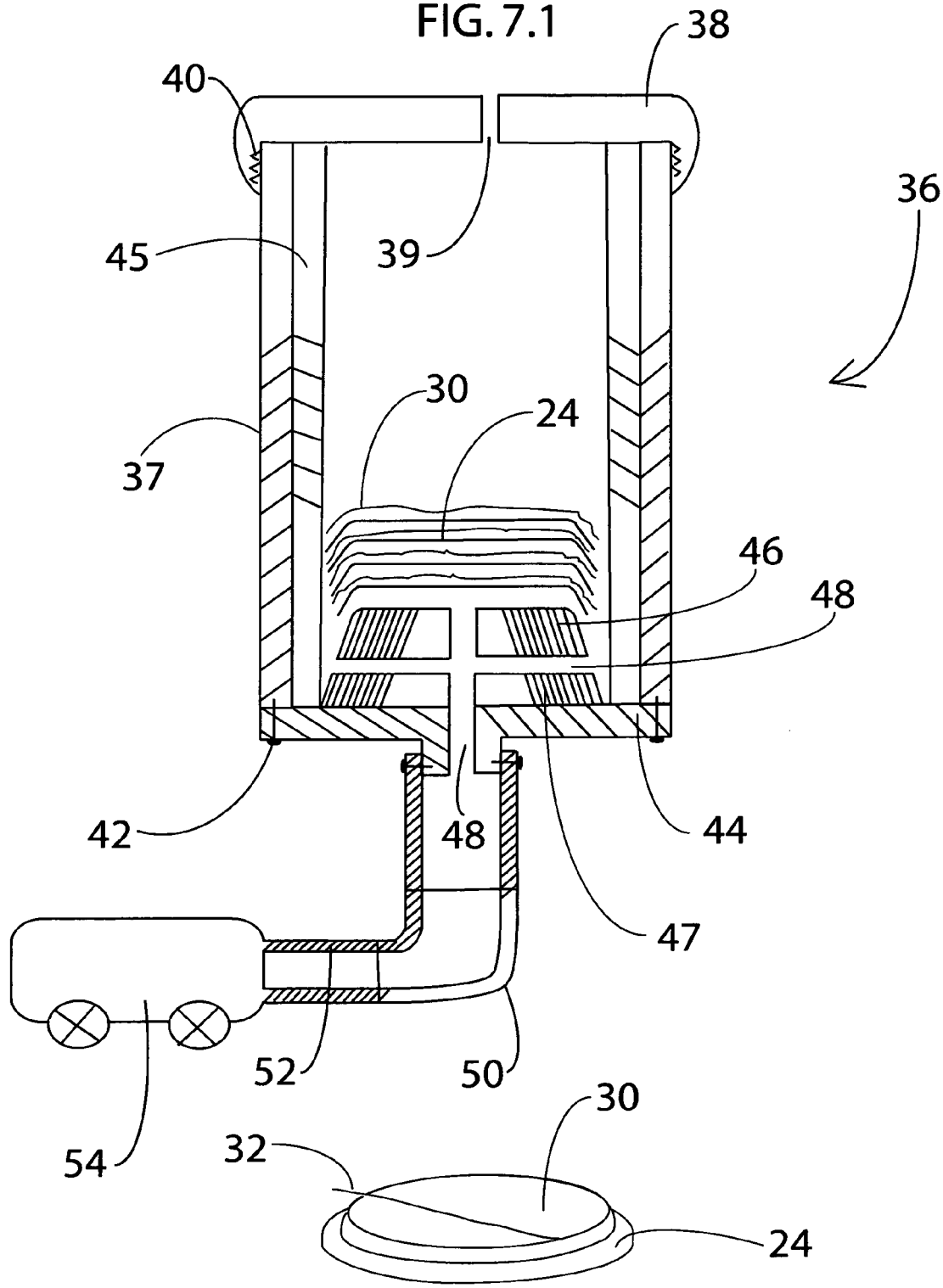

ANTIBACTERIAL PROTECTIVE ENVELOPE

BACKGROUND OF THE INVENTION

This invention belongs to the field of antiseptic devices but more particularly to a protective envelope used to wrap the lid of a cup.

PRIOR ART

The present invention refers to a canadian patent application by the same inventor <<Antibacterial protective cover>> CA 2,710,435 filed on Jul. 28, 2010 which refers to a provisional application U.S. 61/400,027 filed on Jul. 22, 2010.

A study of the prior art has revealed the following:

CN 2599973; Li Bailan and al. published on 2004 Jan. 21 shows a model of a cup with lid used during a journey or on camping and avoiding the introduction of dust, bacteria in the cup. The lid and the cup are threaded to be screwed one onto the other.

GB 2467612; Douglas Hussey; published on 2010 Aug. 11 shows a method of manufacturing a lid which may involve applying a spray of liquid antiseptic material into a receptacle where a drink opening is located. The antiseptic material has the capability of changing to form a protective layer or film covering the drink opening. Part of the production process involves the use of a retractable spray pipe side support and a vacuum holder for the lid.

EP 2 194 003; Dart Container Corporation; published on 2010 Sep. 6 shows a recloseable lid for a drinking cup comprising a cap with a dispensing aperture through which liquid can pass.

OBJECTIVES AND ADVANTAGES

More and more people are worried about the potential risks of contracting diseases in public places like restaurants by drinking in a plastic cup. A lid of a cup is a surface where can settle viruses, bacteria which can cause diseases, such as flu or pharyngitis for example. There is a need on the market for covered cups having a clean lid exempt from bacteria, viruses or any germ.

DESCRIPTION OF OUR CONCEPT

The method in the present invention includes the following steps:
1. An antiseptic fluid, without alcohol, is spread on the top face of a lid of a cup;
2. The lid is dried;
3. A thin membrane of plastic is placed on the top face of the lid. The thin membrane comprises a detachable part located on the zone of opening of the lid, which allows to drink, and is activated by a wire which will be pulled just before drinking.
4. A vacuum is used to stick the membrane to the top face of the lid;
5. Once a consumer is ready to drink, he or she just needs to remove the detachable part by pulling the wire.

The present invention will be further understood from the following description with reference to the drawings.

BRIEF DESCRIPTION OF DRAWING FIGURES

FIG. 1 is a sprayer without alcohol.
FIG. 2 is a plastic lid of a cup.
FIG. 3 is a dryer.
FIG. 4 is a pull wire.
FIG. 5 is a perspective of a plastic film above a plastic lid.
FIG. 6.1 is a bowl of antiseptic liquid with lids thrown inside.
FIG. 6.2 is an operation of drying the lids.
FIG. 6.3 is a plastic film roll.
FIG. 6.4 is a plastic film with its detachable part.
FIG. 7.1 is a vacuum system with lids and plastic films inside.
FIG. 7.2 is a lid with a plastic film over it.

DETAILED DESCRIPTION OF A PREFERRED EMBODIMENT

FIG. 1 shows a vaporizer 20 destined to spray an antiseptic fluid 22 without alcohol.

FIG. 2 shows a lid 24 of a cup with an opening 26 to drink.

FIG. 3 shows a hand held dryer 28.

Figure 5:
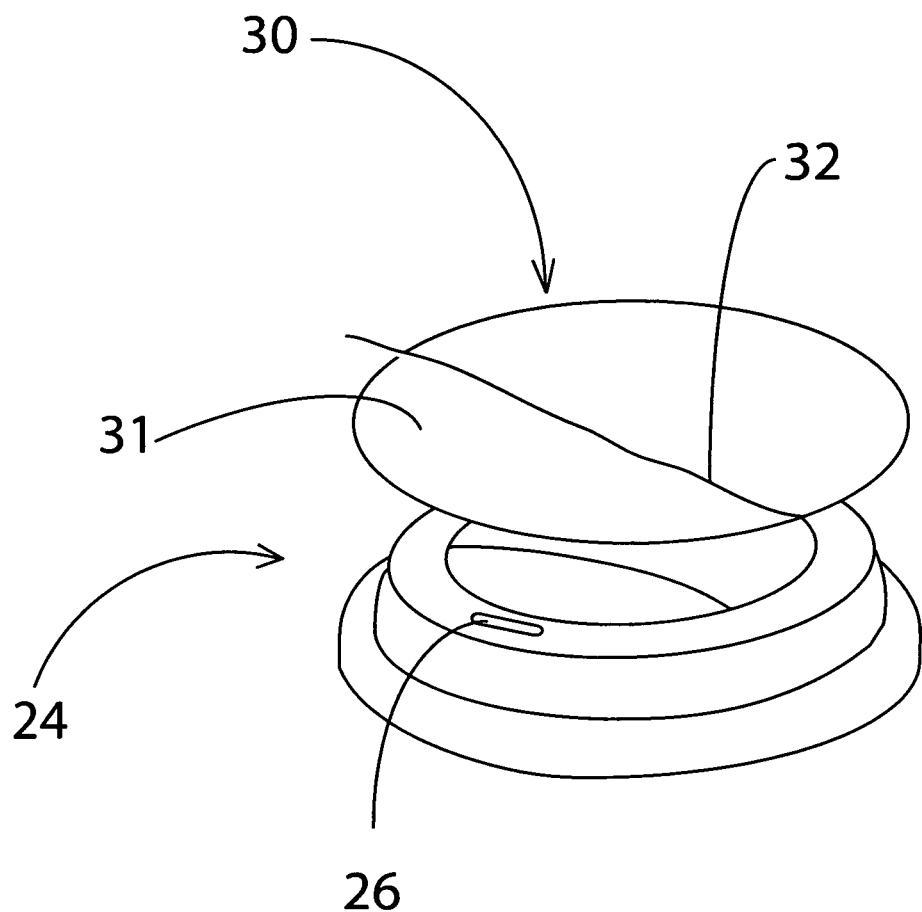

FIG. 4 shows a thin plastic film 30 with a detachable part 31 to be removed by pulling a thread wire 32.

FIG. 5 shows the lid 24 with its top face topped by the thin plastic film 30 having its detachable part 31 positioned above the opening to drink 26 of the lid. One sees also the wire 32 allowing removing the detachable part.

FIG. 6.1 shows a bowl 33 filled with an antiseptic liquid 23 without alcohol and with lids 24 of cups thrown inside to be disinfected.

FIG. 6.2 shows two rows of lids 24 being dried by means of a hand dryer 28'.

FIG. 6.3 shows a plastic roll dispenser 34 such as with a Saran wrap brand.

FIG. 6.4 shows a plastic film 30 with its detachable part 31 to be removed by pulling the thread wire 32.

FIG. 7.1 shows a vacuum apparatus 36 comprising:
an outer shell 37 with a cover 38 at the top and a bottom part 44 fastened to the shell by a screw 42; a lower opening 48 is pierced through the bottom part to allow the passage of air by suction through tubes 52 and bends 50 directed to a vacuum machine 54. The cover 38 appears fastened to the shell by teeth 40. An upper opening 39 may be calibrated to permit a small entry of air from the top to reduce the suction when necessary.

A mould 46 with a base 47 is inside the vacuum apparatus. Lids 24 and plastic films 30 are placed alternatively onto the mould 46. The mould 46 and its base 47 are separated by a channel of air linked in its middle with the opening 48 which ensures the extraction of air from within the interior box of the shell.

A vacuum machine 54 is linked to the opening 48 by the tube 52. The tube has a bend 50.

Inside the box there is a vertical sleeve 45 allowing adjusting the width of the box, the size thereof being such that a little air enters the upper opening 39 and seeps down between the sleeve and the lids and exits the bottom opening 48. When a large number of lids and thin plastic films are present the upper opening may be bigger and bigger.

Teeth 40 and screws 42 are shown on the drawing.

FIG. 7.2 shows the finished product which is the lid 24 with on its superior face the plastic film 30 stuck as a result of the downward suction.

SUMMARY

The present invention discloses a covered antiseptic lid for a plastic cup, such a cup of coffee or a cup of carbonated drinks, such lid having been covered as a result of a five step procedure:

an antiseptic fluid 22, without alcohol, is spread on the top face of the lid 24 of a cup; then the lid is dried;

a thin plastic film 30 is placed on the top face of the lid;

and charged into a vacuum apparatus connected to the suction of a vacuum machine.

The thin plastic film comprises a detachable part located on the zone of opening of the lid which allows drinking, and is activated by a wire which will be pulled just before drinking.

When one is ready to drink, one pulls the thread and the detachable part comes out, freeing the opening where the liquid to drink passes.

It is to be clearly understood that the instant description with reference to the annexed drawing is made in an indicative manner and that the preferred embodiments described herein are meant in no way to limit further embodiments realizable within the scope of the invention. The matter which is claimed as being inventive and new is limited only by the appended claims.

Part
20 Sprayer
22 Antiseptic fluid without alcohol
24 Lid of a cup
26 Opening to drink
28 Dryer
30 Thin plastic film
31 Detachable part
32 Wire
33 Bowl
34 Plastic roll dispenser
36 Vacuum apparatus
37 Outer shell
38 Cover
39 Upper opening
40 Teeth
42 Screw
44 Bottom part
45 Vertical sleeve
46 Mould
47 Base of the mould
48 Lower opening
50 Bend
52 Pipe
54 Vacuum machine

I claim:

1. A combination of a vacuum device with a bundle of lids for plastic cups disposed vertically within a chamber of said vacuum device, each lid being covered by a plastic film, said chamber comprising at the bottom a mold the shape of said lid and the first bottom lid of said bundle being positioned concavely over said mold, said chamber comprising means of extracting air therefrom destined to stick each said plastic film over a corresponding lid, said lid covered by said plastic film being thereby protecting from germ and bacteria;

said vacuum device comprising:

a vacuum machine (54) to suck air;

said chamber (36) comprising an outer shell (37), a cover (38), a bottom (44), a mold (46) placed on said bottom, an opening (48) in said bottom, means of connecting said bottom to said vacuum machine (54); when applying said vacuum, it will empty the air inside said chamber, and will cause said plastic film to stick to said lid.

2. The combination of claim 1 wherein said means of connecting comprise an opening (48) to evacuate air from said bottom, said opening being linked to a pipe (52) comprising a bend (50) and joined to said vacuum machine (54).

3. The combination of claim 2 wherein said lids (24) are for a cup of a form of said mold, and said shell comprises a vertical sleeve that maintains a distance at the periphery of said lids.

4. The combination of claim 3 wherein said mold has an opening (48) to evacuate air through said pipe (52) towards said vacuum machine (54).

5. The combination of claim 3 wherein said cover (38) comprises an opening (39) and teeth (40) to support said shell.

6. The combination of claim 1 wherein said plastic film includes a detachable part to apply above a drink opening of said lid.

7. The combination of claim 6 wherein said detachable part includes a wire to be pulled which allows removing said detachable part from said lid to free said opening to drink.

* * * * *